United States Patent [19]

Davis

[11] 4,206,760
[45] Jun. 10, 1980

[54] BEARING COUPLING FOR ENABLING THE TIP OF A CRYOSURGICAL INSTRUMENT TO BE ROTATED INDEPENDENTLY OF INLET AND EXHAUST TUBES

[75] Inventor: Stephen Davis, Naugatuck, Conn.
[73] Assignee: Cryomedics, Inc., Bridgeport, Conn.
[21] Appl. No.: 920,771
[22] Filed: Jun. 30, 1978
[51] Int. Cl.² .............................................. A61B 17/36
[52] U.S. Cl. ................................ 128/303.1; 62/293; 62/514 JT
[58] Field of Search .................... 128/303.1, DIG. 27, 128/399, 400, 401; 62/293, 514 JT

[56] References Cited
U.S. PATENT DOCUMENTS

| | | | |
|---|---|---|---|
| 3,696,813 | 10/1972 | Wallach | 128/303.1 |
| 4,015,606 | 4/1977 | Mitchineu et al. | 128/303.1 |
| 4,018,227 | 4/1977 | Wallach | 128/303.1 |
| 4,074,110 | 2/1978 | Slaughter | 128/303.1 |

FOREIGN PATENT DOCUMENTS 364317  2/1973  U.S.S.R. ............................. 128/303.1

Primary Examiner—Robert W. Michell
Assistant Examiner—Jeffrey W. Tayon
Attorney, Agent, or Firm—Barry Kramer

[57] ABSTRACT

A cryosurgical instrument having a tip which is cooled by the Joule-Thomson expansion of a pressurized gas. The gas is conveyed to the tip by an inlet tube and exhausts through an exhaust tube connected to the rear of a fitting. The tip is connected to the forward portion of the fitting. The rear and forward portions of the fitting are rotatably connected by a bearing coupling which enables the tip to be rotated independent of the inlet and exhaust tubes.

11 Claims, 2 Drawing Figures

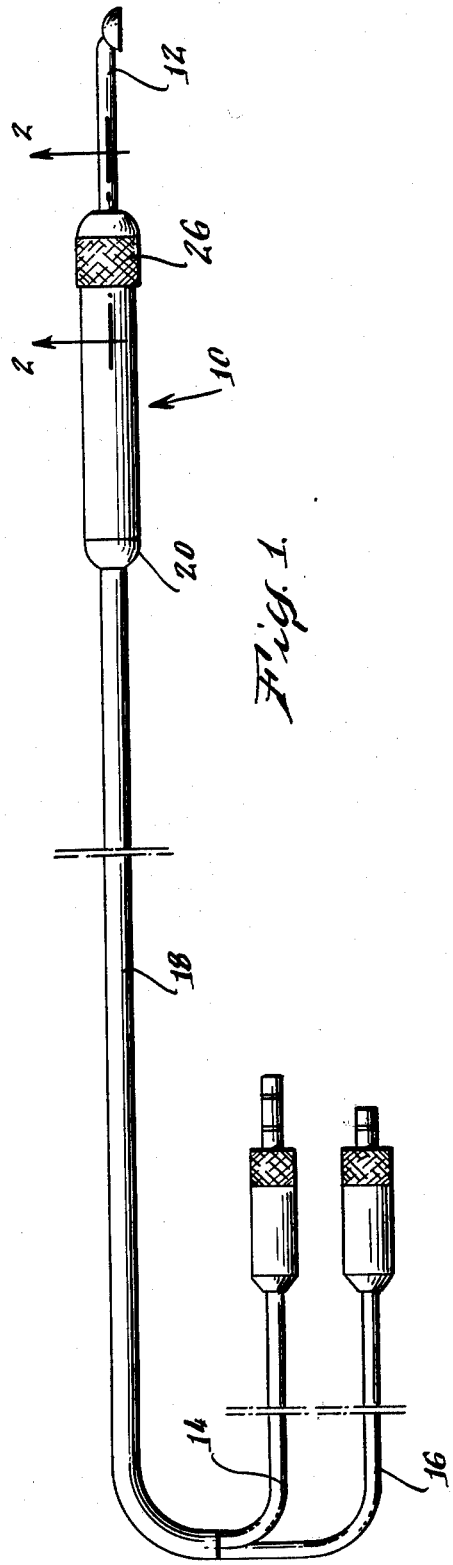
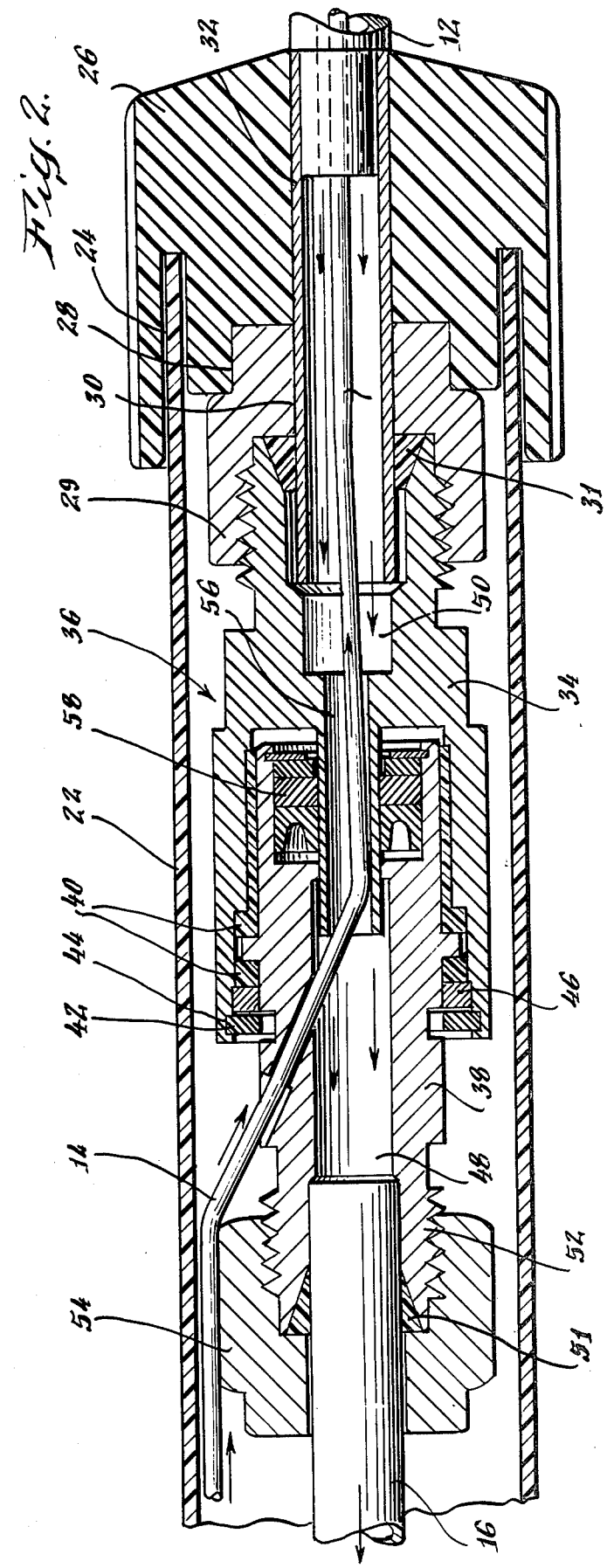

BEARING COUPLING FOR ENABLING THE TIP OF A CRYOSURGICAL INSTRUMENT TO BE ROTATED INDEPENDENTLY OF INLET AND EXHAUST TUBES

BACKGROUND OF THE INVENTION

1. Field of the Invention

This invention relates to a cryosurgical instrument.

2. Description of the Prior Art

In U.S. Pat. Nos. 3,696,813 and 4,018,227 assigned to the same assignee as the present invention, a cryosurgical instrument operating on the Joule-Thomson refrigeration principle is disclosed. Gas under pressure is transported through a narrow orifice to a tip and expanded, cooling the tip. The tip is contacted with tissue to perform various surgical techniques, amongst which are retina attachments or weldments, and other ophthamological procedures. By closing a valve to preclude exhaust of the pressurized gas, back pressure is created in the tip to warm or defrost the tip once the surgical procedure is completed.

With the advent of larger tips for performing such surgical procedures, the inlet and exhaust gas line tubing have had to be increased in diameter to effect sufficient freezing and defrost. This in turn has led to difficulty in manipulating and rotating the tip during surgery, particularly, to place the tip at a proper angle to the eye to perform the required surgery, because the increased diameter tubing is stiffer, opposing ready movement of the tip connected to it.

Accordingly, this invention provides a rotatable tip construction in a cryosurgical instrument operable by a Joule-Thomson expansion of gas through the tip. By providing a rotatable tip, the tip may be properly positioned to perform a particular surgical technique, regardless of the shape of the tip or degree of stiffness of the gas inlet and exhaust lines connected to the tip which tends to oppose ready manipulation thereof.

SUMMARY OF THE INVENTION

In accordance with the invention, a rotatable fitting is threadedly connected between the operating tip and the gas exhaust line of the instrument. The gas inlet line is press-fitted at an angle and extends into and concentrically through the interior of the fitting into the tip. Gas entering the tip will expand through a small orifice or flow restriction in the tip to effect Joule-Thomson cooling of the tip. The gas exhausts back through the hollow fitting to the atmosphere. Suitable valving connected to the exhaust line, when closed, causes back pressure on the gas in the tip to preclude its expansion, thereby warming or defrosting the tip.

The fitting is provided with a forward portion threadedly connected to the tip and a rear portion threadedly connected to the exhaust line and receiving the inlet line therethrough. A bearing structure rotatably connects the forward tip-carrying portion to the rear portion of the fitting enabling the tip to rotate freely relative to the inlet and exhaust lines so the tip can be readily manipulated during surgery.

The fitting can be covered by a knurled bulbous casing connected to the exterior of the tip, which rotates with the tip and serves as a finger grip for the surgeon, and an elongated sleeve slidably disposed within the bulbous casing concentric to the fitting.

BRIEF DESCRIPTION OF THE DRAWING

Further objects and advantages of the invention will become apparent from the following description and claims, and from the accompanying drawing, wherein:

FIG. 1 is a side view in elevation of the cryosurgical instrument of the present invention; and FIG. 2 is a cross sectional view of the instrument taken substantially along the plane indicated by line 2—2 of FIG. 1.

DETAILED DESCRIPTION OF THE PREFERRED EMBODIMENT

Referring now to the drawing in detail, wherein like numerals indicate like elements throughout the several views, the cryosurgical instrument of the present invention is indicated generally by the numeral 10.

Instrument 10 includes a tip 12 for performing an ophthamological surgical procedure. Tip 12 is described in detail in U.S. Pat. Nos. 3,696,813 and 4,018,227, which disclosure is incorporated herein by reference. For purposes of this invention, however, pressurized gas is delivered through an inlet line 14 to a restriction or orifice in the tip 12 and allowed to expand therethrough, cooling the tip via the Joule-Thomson refrigeration effect. The tip is contacted with tissue to perform various cryosurgical operations, such as retina attachments or weldments. The gas, after expansion is vented to the atmosphere through an exhaust line 16. The exhaust line 16 may be connected to a suitable valve (not shown), in a console, which when closed precludes exhaust of the pressurized gas, creating back pressure on the gas in tip 12 to warm or defrost the tip once the surgical procedure is completed.

Inlet line 14 and exhaust line 16 are wrapped in flexible sheathing 18 terminating in a connector 20 in abutment with one end of a cylindrical sleeve 22 forming a housing. The opposite end of sleeve 22 slidably inserted in an annular groove 24 in a knurled bulbous casing 26 connected integrally to tip 12. Casing 26 functions as a finger grip for the surgeon performing an operation with tip 12.

Press-fitted within a bore 28 in casing 26 is a nut 29. Nut 29 includes a central passageway 30 contiguous to a central passageway 32 in casing 26. Tip 12 is press-fitted into passageways 30 and 32. Nut 29 threadedly connects tip 12 and casing 26 to the forward portion 34 of a rotatable fitting 36 housed concentrically within sleeve 22. A flared ferrule 31 between nut 29 and the forward portion 34 of fitting 36 clamps tip 12 against accidental dislodgement and movement.

Fitting 36 includes a concentric rear portion 38 rotatably connected by a Teflon bearing structure 40 to forward portion 34. A snap ring 42 received within an annular groove 44 in forward portion 34, precludes relative axial movement of portions 34 and 38 of fitting 36 by abutment with a backup ring 46 on rear portion 38. Exhaust line 16 is press-fitted into a bore 48 in rear portion 38 which is in line with a bore 50 in forward portion 34. The rear portion 38 includes exterior threads 52 threadedly receiving a clamping nut 54 to assure retention of exhaust line 16 in bore 48 by causing a ferrule 51 to clamp the exhaust line 16 in bore 48.

A tubular, cylindrical connector 56 integral with forward portion 34 provides a radial moving sealing surface between bores 48 and through seal and gasket 58. Inlet line 14 is inserted at an angle through the side wall of the rear portion 38 of fitting 36, through connector 56 and bore 50 onto contiguous passageways 30, 32 and then to the tip 12.

In operation, gas (as indicated by the arrows in FIG. 2), will flow from a source through inlet line 14 to tip 12, expand to cool tip 12, and exhaust from the tip concentrically about inlet line 14 through passageways 32, bore 50, connector 56, bore 48 and exhaust line 16. Closing of a valve upstream from fitting 38 will cause the tip 12 to defrost or warm due to the back pressure on the exhaust gas.

Tip 12 can be rotated relative to inlet line 14 and exhaust line 16 by rotating casing 26 integrally connected to tip 12 and the forward portions 34 of fitting 36 due to the relative rotational connection through bearing structure 40 of forward portion 34 of fitting 36 to the rear portion 38. Rear portion 38 is fixed to, supports and holds exhaust line 16 and inlet line 14. Inlet line 14, in turn, is concentrically positioned relative to forward portion 34, casing 26 and tip 12.

Due to the relative rotation of tip 12 with respect to the inlet line 14 and exhaust line 16, the diameter and stiffness of the tubing used to form the lines is immaterial, as the tip 12 can be rotated and manipulated independent thereof. This enables a sufficient volume of gas to be supplied to the tip 12 to effect Joule Thomson cooling and subsequent defrost of the tip.

What is claimed is:

1. A cryosurgical instrument comprising:
a housing,
a hollow fitting disposed entirely within said housing having a forward and rear portion;
means rotatably connecting the forward portion of said fitting to the rear portion of said fitting, and including means carried by said forward and rear portions for preventing movement of said forward and rear portions in either direction along their respective axes of rotation upon rotation of said forward portion relative to said rear portion;
gas inlet means and gas exhaust means connected to the rear portion of said fitting;
a surgical tip connected to the forward portion of said fitting in communication with said gas inlet means and gas exhaust means; and
means within said surgical tip between said gas inlet means and gas exhaust means for effecting a Joule-Thompson expansion of gas received from said gas inlet means and exhausted through said exhaust means to cool said tip.

2. The instrument of claim 1 wherein said housing includes a knurled bulbous portion connected to said tip.

3. The instrument of claim 2 wherein said housing includes a sleeve covering said fitting received within said bulbous portion.

4. The instrument of claim 3 wherein said bulbous portion is rotatable relative to said sleeve.

5. The instrument of claim 1 including means for threadedly connecting said tip to the forward end of said fitting.

6. The instrument of claim 1 including means for threadedly connecting said gas exhaust means to the rear portion of said fitting.

7. The instrument of claim 1 wherein said gas inlet means is inserted into the rear portion of said fitting from the side thereof.

8. The instrument of claim 1 wherein said gas inlet and gas exhaust means each include
a tube, and
said housing including
a knurled bulbous portion connected to said tip; and
a sleeve covering said fitting slidably received within an annular groove in said bulbous portion; and
a flexible sheathing covering said inlet and exhaust tubes in abutment with said sleeve.

9. The instrument of claim 1 wherein said forward and rear portion of said fitting includes a bore therethrough and a stationary connector tube is positioned between said bores to provide communication therebetween, said gas inlet means extending through said bores and connector tube and terminating in said tip.

10. The instrument of claim 1 wherein said means for preventing movement of said forward and rear portions carried by said forward and rear portions of the fitting includes:
a ring shaped member carried by either said forward or rear portion, and
an annular groove in the other of said forward or rear portions for slidably confining said ring shaped member therein.

11. The instrument of claim 10, wherein:
said ring shaped member is carried by said rear portion, and
said annular groove is defined in said forward portion.

* * * * *